US008600769B2

(12) United States Patent
Drucker et al.

(10) Patent No.: US 8,600,769 B2
(45) Date of Patent: Dec. 3, 2013

(54) MEDICAL BILL ANALYSIS AND REVIEW

(75) Inventors: Vincent Drucker, Dallas, TX (US); Larry Mattingly, Keller, TX (US); Kevin Hatchett, Plano, TX (US); Bob Katen, Keller, TX (US); Trevor Davis, Irving, TX (US)

(73) Assignee: FairPay Solutions, Inc., Addison, TX (US)

( * ) Notice: Subject to any disclaimer, the term of this patent is extended or adjusted under 35 U.S.C. 154(b) by 1505 days.

(21) Appl. No.: 11/124,938

(22) Filed: May 9, 2005

(65) Prior Publication Data
US 2005/0273360 A1    Dec. 8, 2005

Related U.S. Application Data

(60) Provisional application No. 60/572,433, filed on May 19, 2004.

(51) Int. Cl.
*G06Q 50/00* (2012.01)
*G06Q 10/00* (2012.01)

(52) U.S. Cl.
USPC .................................................. 705/2; 705/4

(58) Field of Classification Search
USPC ........................................................... 705/2
See application file for complete search history.

(56) References Cited

U.S. PATENT DOCUMENTS

| | | | |
|---|---|---|---|
| 4,491,725 A | * | 1/1985 | Pritchard .......................... 705/2 |
| 5,956,687 A | | 9/1999 | Wamsley et al. |
| 6,826,536 B1 | * | 11/2004 | Forman ............................. 705/4 |

OTHER PUBLICATIONS

Reinsel, Elements of multivariate time series analysis, 1993, Springer series in statistics, p. 1-2.*
Harvey, Forecasting, structure time series models, 1990.*
Pope, Cost of practice and geographic variation in Medicare fees, Health Aft (Millwood). 1989 Winter;8(4):206-7.*
Andrew C. Harvey, "Forecasting, Stuctural time Series Models and the Kalman Filter", Cambridge University Press 1989.

* cited by examiner

*Primary Examiner* — Tran Nguyen
(74) *Attorney, Agent, or Firm* — Howison & Arnott, L.L.P.

(57) ABSTRACT

A method and business technique for reviewing medical service provider bills, recalculating and providing payment recommendation to a paying party for the bills. The method includes analyzing medical bills and determining erroneous and inappropriate charges on bills. The method provides a payment recommendation using multiple databases and sophisticated mathematical modeling that includes one or more of the following: a medical service provider's actual cost of delivering the medical services provided; the average profit-margin of that provider, an average profit margin of comparable medical providers in an area, other industry-specific profit-margin benchmarks; an average acceptable payment by medical service providers in the area for comparable services; payment rates negotiated by large health insurers and managed care organizations; and other industry benchmarks for reasonable payment for comparable services.

18 Claims, 2 Drawing Sheets

MEDICAL BILL ANALYSIS AND REVIEW

RELATED APPLICATION

This application is a Utility Application of U.S. Patent Provisional Application Ser. No. 60/572,433, filed on May 19, 2004, which is incorporated herein by reference in its entirety.

BACKGROUND OF THE INVENTION

1. Technical Field of the Invention

The present invention relates in general to reviewing medical related bills. In particular, the present invention relates to a method and business technique for reviewing medical service provider bills, re-calculating the same and providing a payment recommendation for the bills.

2. Description of Related Art

In the United States today, health care charges are skyrocketing. The days of a single family practice doctor or nurse typing medical bills for services rendered are gone. Even small offices and clinics have all changed to computer billing. In large clinics and hospitals, the billing departments are virtually (if not entirely) separate from the actual process of doctors and nurses providing medical care. The people working in billing departments may have no medical backgrounds and are mainly concerned with generating bills for medical services and collecting money for the same. The bills sent out by the billing department can be complicated. Often the billing department personnel cannot provide a proper explanation for the charges since the procedure codes used in the bills are created by others (e.g. the medical records department or medical staff where the services are rendered) and the charges for the services and items provided are generated from multiple sources (check-off sheets, swiped bar codes on supplies, pharmacy dispensing records, automated rules, etc.). The medical bills are not designed for a patient to understand and there is no system set up to make it convenient for a patient to ask questions, get information or even have someone adjust errors in a medical bill.

Most hospitals and other health care facilities, such as ambulatory surgical centers (ASCs), charge patients for medical services and supplies when they are ordered, not when they are received by the patient. If a doctor's order changes and the services/or supplies are not used by the patient, the charges may remain on the bill in error. Many hospitals and other facilities charge a standard list of services and items based on the procedure performed (e.g. a simple emergency visit), a daily rate (e.g. what is being used in one day in an intensive care unit), or some other similar unit of service regardless of what items or services were actually provided. (commonly called procedure-based charging, per-diem based charging, surgery cart-based charging, etc.) Similarly, if the patient is discharged from a hospital sooner than anticipated, the patient may be billed for services they never actually received. Many facilities bill the same charges multiple times: one time in an all-inclusive facility charge (ICU, recovery, operating room, etc.); a second time some of the items are charged for separately such as supplies and medication and equipment, and a third time items previously charged in the all-inclusive facility charges and itemized charges may, again, be charged as surgical trays, packs and other pre-made packages. Other factors that contribute to improper billing are human errors (e.g., keystroke errors), complicated billing systems and duplicate billings caused by different departments entering the same medical procedures, items that were used being charged to the wrong patient, etc.

Since the advent of Medicare, in the 1960ies during the Johnson presidency, there have been a series of initiatives by governmental and other payers to control the rising costs of medical care and to counter various "creative" charging practices by facilities and medical providers. The Federal Government and State Governments have primarily tried to control costs through various initiatives that control the payments for services rendered and counter various "creative" charging practices and, to a lesser extent, ration care by not paying for treatments that they consider to be inappropriate or experimental. Insurance companies and other group health payers have adopted a multi-faceted strategy known as managed care. In addition to controlling the prices they pay, under managed care insurance companies use other "managed care" methods including sets of rules that specify, for a given injury, the type of treatments and the quantity of such treatments that the payor will pay.

The Federal Government has adopted various payment protocols that today pay almost entirely according to set schedule of fees for the specific services rendered by different types of providers and facilities. The State Governments, when they regulate the appropriate payment for medical services for worker injured and/or auto accident injured victims, also largely use fee schedules. The very large insurance companies who are providing health insurance largely to employer-sponsored groups, also have adopted fee schedules. These are usually variants of the payment methodology researched and developed by the Federal Government.

The Centers for Medicare and Medicaid Services (CMS) is the Federal agency responsible for the operation and oversight of federally-funded Medicare and Medicaid medical insurance programs. These medical insurance programs handle the medical claims submitted by health care providers, such as doctors, hospitals. The medical insurance programs then reimburse claims that are valid. To stop intentional and unintentional over billing, Medicare has implemented various rules and controls that place an enormous burden upon health care providers to code and bill in accordance with Medicare's stringent and ever-changing rules.

Preferred Provider Organizations (PPOs) are often used by payers which cover smaller numbers of employees and groups. PPOs negotiate discount payment agreements with providers, in return for promising to channel more patients to the provider. PPO agreements typically specify a discount from billed charges or "Usual, Customary & Reasonable" charges.

There is a large and growing number of patients whose payments are not subject to the fee schedule rates mandated by Federal and State governmental authorities nor are they able to access the reduced fees negotiated by large insurance companies.

There has been aggressive pricing and manipulation of charges by providers that disadvantages these patients who are outside one of theses large payor systems. While the large payor systems pay roughly 66% of professional's "Usual, Customary and Reasonable (UCR) charges and around 37% of the UCR charges by facilities, those patients who are outside these systems are being asked to pay 100% of the providers' and facilities' charges.

SUMMARY OF THE INVENTION

An embodiment of the present invention includes a method for reviewing medical service provider bills, re-calculating the bills and providing a payment recommendation for the bills. In accordance with an embodiment of the invention, there is provided a method for reviewing medical bills. The method comprises analyzing the medical bills and determining erroneous charges on the medical bills and then eliminating the charges for the erroneous billings.

In accordance with another embodiment of the invention, a method for recalculating medical bills comprises analyzing the medical bills and determining erroneous charges on the medical bills and then eliminating the charges for the erroneous billings, then determining an actual cost of the remaining medical services provided by the medical service providers, and then providing a payment recommendation for the medical bills based upon the actual cost and an area-specific reasonable profit-margin calculation.

In accordance with another embodiment of the invention, a method for recalculating medical bills includes analyzing the medical bills, identifying errors in the medical bills and then eliminating the erroneous charges on the medical bills then determining the price being paid, on average in the area for comparable services, for the remaining medical services billed by the medical service professional providers or facilities The method may further comprise providing a payment recommendation for the medical bills based upon the application of mathematical multivariate time series models and Kalman filters.

BRIEF DESCRIPTION OF THE DRAWINGS

For a more complete understanding of the present invention, reference is made to the following detailed description taken in conjunction with the accompanying drawings, wherein.

Figure 1:
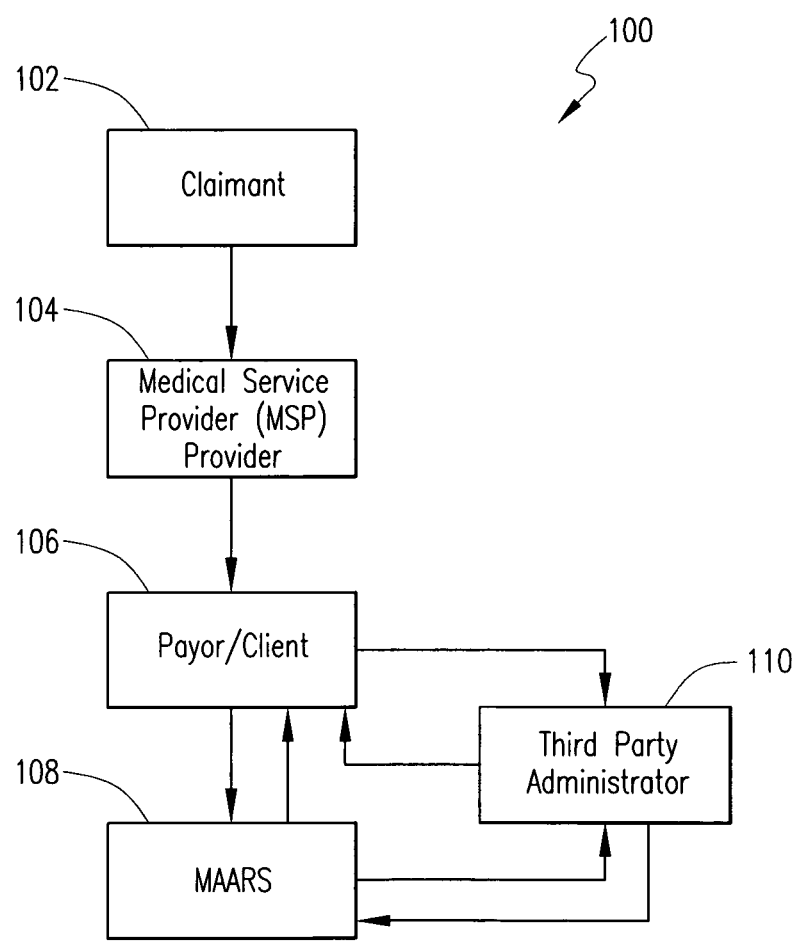
FIG. 1 is a block diagram that shows pertinent details of an exemplary Medical Analysis and Review Services method, in which the present invention can be implemented.

DETAILED DESCRIPTION OF THE
EXEMPLARY EMBODIMENTS OF THE
INVENTION

An exemplary embodiment of the invention, referred to as Medical Analysis And Review Service (MAARS), forecasts future and present day medical service provider costs based on past, recent and historical medical cost information. Various techniques can be utilized to forecast future and present day costs including mathematical algorithms that have never before been applied to or used in medical cost estimations.

One of the most common issues facing the Medical Service Providers (MSP's) and the entities responsible for reimbursing the MSP's is the issue of what amount is an appropriate amount to be charged by the MSP's to the reimbursing parties. An exemplary MAARS method provides an objective process for assuring that the bill for medical services, supplies or medications charged by MSP's are paid reasonably. An embodiment of the MAARS method utilizes multivariate time series analysis based upon:

1. Legal and regulatory findings to date in the applicable jurisdiction;
2. Cost of providing the service for comparable providers in a particular geographic region;
3. The average reimbursement being paid by all payors to medical service providers in a particular geographic region for comparable services;
4. Reasonable charges for the actual and appropriate services provided in a particular geographic region;
5. Cost to that provider for rendering the service;
6. Average profit margin for that provider; and
7. Average profit margin for comparable providers in the area.

An exemplary MAARS method is state-specific pursuant to each state's legislative records, published guidelines, rules, administrative notices and each state's case laws. In addition, the exemplary MAARS method utilizes applicable federal legislative records, published records, published guidelines, rules, administrative notices and federal case laws. Furthermore, the exemplary MAARS method uses a plurality of databases and mathematical algorithms that have never before been applied to or used in medical pricing estimations to determine a reasonable amount to pay for medical bills.

MSP's generally use several types of procedure codes. The procedure codes specify the medical procedures ordered. The first type of code is called a Common Procedural Terminology (CPT) code, which was developed by the American Medical Association (AMA). The second type of CPT code is a Health Care Procedural Coding System (HCPCS), which was developed by Health Care Financing Administration (HCFA) to address issues with the CPT codes as they relate to medical billing. More specifically, each CPT code indicates a set of related medical procedures that can be ordered. Two other sets of codes are from the International Classification of Diseases (ICD). The third type of code used in the United States is ICD procedure code, which also indicate the procedures ordered. The fourth type of code is ICD diagnosis codes that specify and classify the injury or disease or illness of the patient. CPT and ICD codes can represent a simple procedure or a more complex procedure.

In many instances, medical bills from MSP's include overcharges. An overcharge is a charge over the accepted charge for the medical treatment or for other additional medical issues not specifically approved by the reimbursing party. There are several ways by which MSP's overcharge patients for medical services provided. According to an exemplary embodiment, a patient can be mistakenly billed for medical services that were never provided to the patient. Therefore, it is extremely important to request all medical records, pharmaceutical records and itemized bills from the MSP's. As an example, the medical records may show results of six blood tests while the patient is being charged for nine blood tests. Another frequent error is a duplicate bill in which the patient is billed twice for a service rendered only once.

A medical bill may include phantom charges by the MSP's. More specifically, some MSP's computer software may automatically bill for a variety of items and services ordinarily associated with a particular service regardless of whether the services or items were actually used on that patient. As an example, if the patient is billed for a childbirth, there should be no charges for sedation unless the patient actually received sedative drugs because it is not a normal medical practice to give a patient, who is birthing a child, sedatives.

Often times, MSP's overcharge for the quantity of items provided. For example a common error occurs with respect to intravenous (IV) solutions that are administered to the patient on the day of admissions to the MSP (e.g., a hospital). The hospital computer normally bills the patient for a full day's worth of IV solutions. However, if the patient was admitted to the hospital late in the day, the patient may receive only a few hours worth of IV solutions.

Proper billing procedures require MSP's to "bundle" related charges for a particular medical procedure. As an exemplary embodiment, the charge for removing an appendix will include the operating room, operating utensils and all other goods, services and medications normally related to this operation. "Unbundling" occurs when the MSP's separate some of the charges that should be included in the "global" bundle charge for the operation, thus, duplicating some of the charges. As an example, a bill for an appendectomy may wrongly include separate charges for the pre-operative physical, such as drawing blood, cardiogram and interpretation of the cardiogram.

Overcharges on medical bills may also result from excessive mark-ups from MSP's. As an exemplary situation, the patient may be billed $ 75 for a laxative or $30 for a thermal therapy kit. In particular, drugs, supply items, or care charges are often excessively marked-ups. According to yet another situation, some hospitals charge much more for comparable services than other hospitals in the same geographic region.

In some instances, medical bills from the MSP's are upcoded. More specifically, the MSP's use inappropriate CPT/ICD codes related to more complicated procedures than the procedures that were actually performed. The MSP's use CPT/ICD codes on medical bills that relate to much more elaborate procedures which would enable the MSP's to bill for larger reimbursements. In general MSP's might use more expensive CPT/ICD codes to perform a service that required a lesser expensive CPT/ICD code. Other issues that may cause inflated bills may result from overstaffing a surgical procedure, unnecessary delays caused by MSP errors which may result in longer stay, surgical delays etc.

An exemplary MAARS method overcomes the discrepancies in medical bills discussed above. An exemplary MAARS method utilizes cost-based methodology by analyzing the medical bills generated by the MSP's. An exemplary MAARS method verifies that the MSP's use appropriate CPT/ICD codes, identifies potential "unbundling" errors, duplicate, incorrect and "exploded" charges, identifies items and services that were never provided, identifies excessive and/or inappropriate procedures, determines the actual cost of the medical services rendered and establishes a suggested reasonable amount of reimbursement for the medical bills, the details of which will be discussed later.

According to an exemplary MAARS method services embodiment, services rendered by Ambulatory Surgical Centers (ASC's) may also be analyzed for proper and improper billing amounts. An ASC is a free standing surgical facility licensed as a surgical center under state laws. Since very few states regulate how ASC's charge for their services, the bill for medical services or supplies charged by ASC's can be astronomical. An exemplary MAARS method delivers an objective process for assuring that the bill for medical services or supplies charged by ASC's are analyzed and paid reasonably.

According to another exemplary embodiment of the present invention, an exemplary MAARS method also analyzes medical bills for Inpatient and Outpatient services rendered by MSP's. Inpatient medical care refers to treatment provided to an individual admitted as a bed patient in a hospital or any other medical facility where room and board charges are incurred. Outpatient medical care refers to treatment provided to an individual without having to be admitted to a hospital or any other medical facility. An exemplary MAARS method delivers an objective process for assuring that the bill for medical services or supplies charged for Hospital Inpatient and Outpatient services are analyzed and paid reasonably.

In yet another embodiment, an exemplary MAARS method is used for recalculating and providing payment recommendations for other medical bills including, but not limited to, services by physicians, chiropractors, pharmacies, medical supplies, durable medical equipment, etc. An exemplary MAARS method also may be utilized to analyze and recalculate medical bills for services rendered by all other MSP's.

An exemplary MAARS method is used for recalculating and providing payment recommendations for medical bills originating from auto or group health insurance service and/or providers of health care services to other payers. Additionally, an exemplary MAARS method is also applied and used to quantify workers compensation related bills. In the workers compensation area, most states have fee schedules that dictate the reimbursement amount for a particular medical service procedure provided by MSP's. In general, medical bill recalculation only reduces medical service provider bills to amounts permitted under the fee schedules. However, the present fee schedules are not comprehensive. The exemplary MAARS method provides a detailed, comprehensive, and novel process for recalculating medical service provider bills to a reasonable amount where the fee schedules do not apply or the rules for applying them allow for providers to manipulate the billing to get additional payments.

Referring now to FIG. 1, there is illustrated a block diagram that shows pertinent details of an exemplary Medical Analysis and Review Services method 100 that will be used to describe the life cycle of a medical bill in accordance with the present invention. In the block diagram, a claimant 102 refers to an individual receiving medical care. A provider 104 refers to a medical service provider rendering medical services to the individual (e.g., hospitals, doctors etc). A payor/client 106 refers to a third party entity (commercial or government) that is responsible for reimbursing the medical service provider.

In a typical workers compensation scenario, a claimant 102 suffers a job-related injury. In another exemplary scenario, the claimant 102 can be an individual suffering from an illness, an individual being injured in an auto accident or any individual otherwise requiring medical treatment. The claimant 102 then contacts a medical service provider (MSP) 104 for medical treatment. After diagnosing the injury, the MSP 104 provides necessary medical treatment to the claimant 102. The MSP 104 issues a bill to the payor/client 106 related to the medical services rendered to the claimant 102. According to an exemplary embodiment of the present invention, the payor 106 can be, for example, an insurance company. In another exemplary embodiment, the payor 106 can be a self-insured person or any other entity responsible for reimbursing the provider 104. The payor 106 reviews the medical bills submitted by the MSP's 104 and processes the bill through their standard bill review system. The payor 106 forwards the bill for specialty bill review 108, either directly or through another agent such as a Third-Party Administrator (TPA) 110.

According to an exemplary embodiment of the present invention, the medical bills are sent to an exemplary MAARS service where the bills are scanned into a MAARS system. In another exemplary embodiment, the medical bills received at a MAARS service are inspected manually. In another exemplary embodiment, the medical billing information is received electronically. After receiving the bills from the payor 106 or TPA 110, the exemplary MAARS service determines if the bills received are eligible for specialty review. A specialty review applies where the jurisdiction's laws and regulations do not define a specific payment amount for the medical services described in the MSP's itemized bill. The criteria for specialty review will vary by the type of payer and their need to have the medical bills, for which they have a payment obligation, reviewed for determining a payment recommendation. For workers' compensation payers, it may typically be bills over $1000 where the state or Federal fee schedules do not apply, or the rules for applying them allow for providers to manipulate the billing to get additional payments. For payers of first party auto medical claims, it may typically be bills over $1000 in the states where payers have a first party liability in excess of $10,000 and there are no applicable fee schedules, or the rules for applying them allow for providers to manipulate the billing to get additional payments. For payers of third party auto medical claims, it may typically be bills over $1000 for policies where they have a liability in excess of $5,000 and there are no applicable fee schedules, or the rules for applying them allow for providers to manipulate the billing to get additional payments. For group health payers, it may typically be all bills where the applicable payment formula is susceptible to MSP manipulation of the billing to get additional amounts. If the bills are not eligible for the specialty review, they are sent back to the payor 106. However, if it is determined that the bills are eligible for specialty review, the exemplary MAARS system 108 uses a variety of rules to screen bills for inappropriate charges and a mathematical multivariate time series analysis for analyzing the remaining billed charges and for providing a recalculated payment recommendation for the remaining billed charges.

The exemplary MAARS system reviews the medical bill extensively to make sure that appropriate CPT/ICD codes have been assigned to the medical bill. In addition, the MAARS system ensures that the medical bill does not include duplicate charges, incorrect charges, "exploded" charges, "unbundling," and other billing errors. Furthermore, the exemplary MAARS system reviews the medical bill to determine if there are any other discrepancies present on the medical bill. The exemplary MAARS system further may require that the medical bills are reviewed by a third party with medical training and/or computerized systems for any questionable charges. More specifically, the third party with medical training and/or computerized systems review the bill to inspect for charges that are either unrelated to the patient's treatment for a particular injury, for items and services that were never provided or for any unorthodox, controversial, inappropriate, or excessive procedures billed. After the bills have been thoroughly reviewed, the exemplary MAARS system determines what are the acceptable charges for the medical services rendered that should be paid, based on predetermined criteria. The MAARS system recalculates the bill and recommends a reasonable amount of payment to the MSP for the medical bill.

The exemplary MAARS method is state-specific pursuant to each state's legislative records, published guidelines, rules, administrative notices and each state's case laws. In addition, the MAARS method utilizes applicable federal legislative records, published records, published guidelines, rules, administrative notices and federal case laws. Furthermore, an exemplary MAARS method uses a plurality of national and state reference standards, that have been analyzed and mathematically modeled using multivariate time series analyses to become exemplary databases used to determine a reasonable amount of reimbursement to pay for medical bills. The reimbursement amount includes the calculated actual cost of medical services provided by the MSP's as determined by the MAARS system, along with a reasonable profit-margin for providers in the area. The exemplary MAARS system reviews the MSP's publicly filed Medicare cost reports and may use these to determine the MSP's profit margin and other statistical analyses. The exemplary MAARS system applies a statistical trending analysis to the MSP's own reported numbers to determine the MSP's average profit margins. The exemplary MAARS system then applies this analysis to similar MSPs in the same geographic area for the same services to determine what the average profit margins would be for the community. The reasonable profit margin is developed from these figures. After recalculating the bills, MAARS system generates an Explanation Of Review (EOR) for each bill that indicates a recalculated amount of payment deemed appropriate by the MAARS system for paying the MSP's. The EOR is returned back to the payor 106 either directly or through the TPA 110 or another agent of the payer.

A detailed illustration of an exemplary medical bill as issued by an MSP is included as Exhibit A to demonstrate the various portions of a medical bill that is analyzed by an exemplary MAARS system. In order to better understand the medical bill and to eliminate confusion, it is important to note that only certain portions of the bill will be discussed in detail. Reference numeral 202 provides details of the payor. According to an exemplary embodiment of the present invention, a payor refers to a third party entity (commercial or government) that is responsible for reimbursing the MSP's for medical services rendered. Section 202 includes the payor information, a bill ID number, which is used to identify various patients, a bill type, an insurance type, the date the bill was generated and the State in which the medical services were rendered.

Section 204 provides details of the claimant or a person receiving medical services. More specifically, a patient's name, employer information, the patient's social security number and the date when the patient received medical treatments are all illustrated. In addition, a claim number and a patient account number is also shown. Section 206 illustrates pertinent details of the MSP (e.g., hospitals, doctors etc.). More specifically, the information in section 206 includes the name and address of the MSP and their Tax ID. Section 208 refers to a summary of the medical services rendered to the patient along with the codes that identify the various medical services and supplies that were needed towards treating the patient.

Section 210 is an elaboration of section 208 providing a detailed itemized statement of all the procedures performed in treating the patient. The various columns of section 210 illustrate in detail the complete medical services provided by the MSP to the patient. More specifically, columns A and B illustrate the actual date on which the patient was treated along with the actual procedures that were performed to treat the patient. Column C illustrates a procedure code that represents the treatment provided to the patient. Columns D and E provide information related to the total quantity of items utilized during the treatment of the patient. The items may relate to any products that were needed for treating the patient (e.g., IV solution, drugs, supplies etc). Column G represents the total amount billed by MSP's for the patients treatment corresponding to the particular services provided in treating the patient as shown in column B.

In many cases, medical bills from the MSP's may have overcharges. Details of the various ways MSP's overcharge have been described in detail above. In several instances, before reimbursing the MSP's, a payor may send the medical bills for specialty review via the MAARS method. An exemplary MAARS method delivers an objective process for assuring that the bill for medical services or supplies charged by MSP's are reasonable or should be adjusted to a reasonable amount for payment. The MAARS method utilizes mathematical multivariate time series analysis based upon:

1. Legal and regulatory findings to date;
2. Cost of providing the service for comparable providers in a particular geographic region;

3. The average reimbursement being paid by all payors to medical service providers in a particular geographic region for comparable services;
4. Reasonable charges for the actual and appropriate services provided in a particular geographic region;
5. Cost to that provider for rendering the service;
6. Average profit margin for that provider; and
7. Average profit margin for comparable providers in the area.

An exemplary MAARS method is state-specific pursuant to each state's legislative records, published guidelines, rules, administrative notices and each state's case laws. In addition, a MAARS method utilizes applicable federal legislative records, published records, published guidelines, rules, administrative notices and federal case laws. Furthermore, the MAARS method uses a plurality of exclusive databases and mathematical algorithms that have never before been applied to or used in medical pricing estimations to determine a reasonable amount to pay for medical bills. MAARS method reviews the medical bills and provides payment recommendation for the bills as illustrated in column H of Exhibit A. Column I illustrates the recalculated amount recommended by the MAARS method for paying the MSP's. Moving now to the bottom of page 3 of the medical bill, reference numeral 212 represents the total amount billed by the MSP's for treating the patient. However, after the specialty review by the MAARS method, the recalculated and suggested amount due to the MSP's is represented by reference numeral 214. The amount represented by reference numeral 214 (as recommended by the MAARS method) includes the cost of the services to the MSP plus a reasonable mark-up (profit) for services provided by the MSP's.

According to an exemplary embodiment of the MAARS method, the method utilizes various mathematical multivariate structural time series models and applies Kalman filters where appropriate. The mathematical multivariate structural time series models are enormously powerful tools which open the way to handling a wide range of data. A strong feature of time series models used in conjunction with state-space models is the usage of an algorithm for filtering, smoothing and predicting. A state-space model is a two-layer model. An external layer involves an observed process y. This process is assumed to follow a measurement equation:

$$y_t = Z_t \alpha_t + d_t + \epsilon_t$$

For each t, $y_t$ is a n-vector. The n*m matrix $Z_t$ is a matrix of regressors, while $\alpha_t$ is the regression coefficient. The vectors $\epsilon_t$ are independent multi-normals with zero mean and covariance $H_t$.

The internal layer involves the unobserved process $\alpha$. The process is assumed to follow the transition equation:

$$\alpha_t = T_t \alpha_t + c_t + R_t n_t$$

Here $T_t$ is an m*n matrix, $R_t$ is an m*q matrix and the components of white noise $n_t$ have a multi-normal distribution with zero mean and covariance matrix $Q_t$. The process is initiated with a random vector $\alpha_o$, which has a mean of $a_o$ and a covariance matrix of $P_o$.

The elements $Z_t$, $d_t$, $H_t$, $T_t$, $c_t$, $R_t$, and $Q_t$ are referred to as the system matrices. If the system matrices do not change in time the system is said to be time-invariant or time homogeneous. The system is also stationary for a specific selection of $a_o$ and $P_o$.

Once the data has been put in state space form, the Kalman filter may be applied which in turn leads to algorithms for prediction and smoothing. The Kalman filter also opens the way to a maximum likelihood estimation of unknown parameters in a model. This is achieved via prediction error decomposition. Thus, a Kalman filter can be used to access and predict cost of medical services based on acceptable data associated with such services or similar services.

The Kalman filter is a recursive procedure for computing an optimal estimator of a state vector at time t, based on information available at time t. In certain engineering applications, the Kalman filter is important due to on-line estimations. The current value of a state vector is of prime interest (for example, the vector may represent the coordinates of escalating charges from the medical service provider) and the Kalman filter enables the estimate of the state vector to be continually updated as new observations become available.

Another reason for the importance of Kalman filter is that when disturbances and initial state vectors are normally distributed, the Kalman filter enables likelihood function to be calculated via what is known as a prediction error decomposition. This opens the way for the estimation of any unknown parameters in the model. The Kalman filter also provides the basis for statistical resting and model specification.

The Kalman filter is an efficient recursive algorithm for the computation of the optimal estimator $a_t$ and $\alpha_t$, given the information up to (and including) t. A by product is the computation of the error in estimation:

$$P_t = E[(\alpha_t - a_t)(\alpha_t - a_t)']$$

Suppose that at time t−1, $a_{t-1}$, and $P_{t-1}$ are given. The algorithm then computes the predicted values with the prediction equations:

$$\alpha_{t/t-1} = T_t a_{t-1} + c_t$$

$$P_{t/t-1} = T_t P_{t-1} T_t' + R_t Q_t R_t'$$

The corresponding predicted $y_t$ is $$\hat{y}_t = Z_t \alpha_{t/t-1} + d_t$$

The mean square error (MSE) of the innovation $v_t = y_t - \hat{y}_t$ is $$F_t = Z_t P_{t/t-1} Z_t' + H_t$$

Once the new observation $y_t$ becomes available, the estimates of the state can be updated using the updating equations:

$$a_t = \alpha_{t/t-1} + P_{t/t-1} Z_t' F_t^{-1}(y_t - Z_t \alpha_{t/t-1} - d_t)$$

$$P_t = P_{t/t-1} - P_{t/t-1} Z_t' F_t^{-1} Z_t P_{t/t-1}$$

As such the Kalman filter is used in a novel technique to predict costs of medical procedures based on cost information of similar medical procedures. The Kalman filter can be used to accurately estimate a cost of a new medical procedure. The Kalman filter may also be used to predict a MSP's actual cost of an unlisted or unusual medical procedure.

Figure 2:
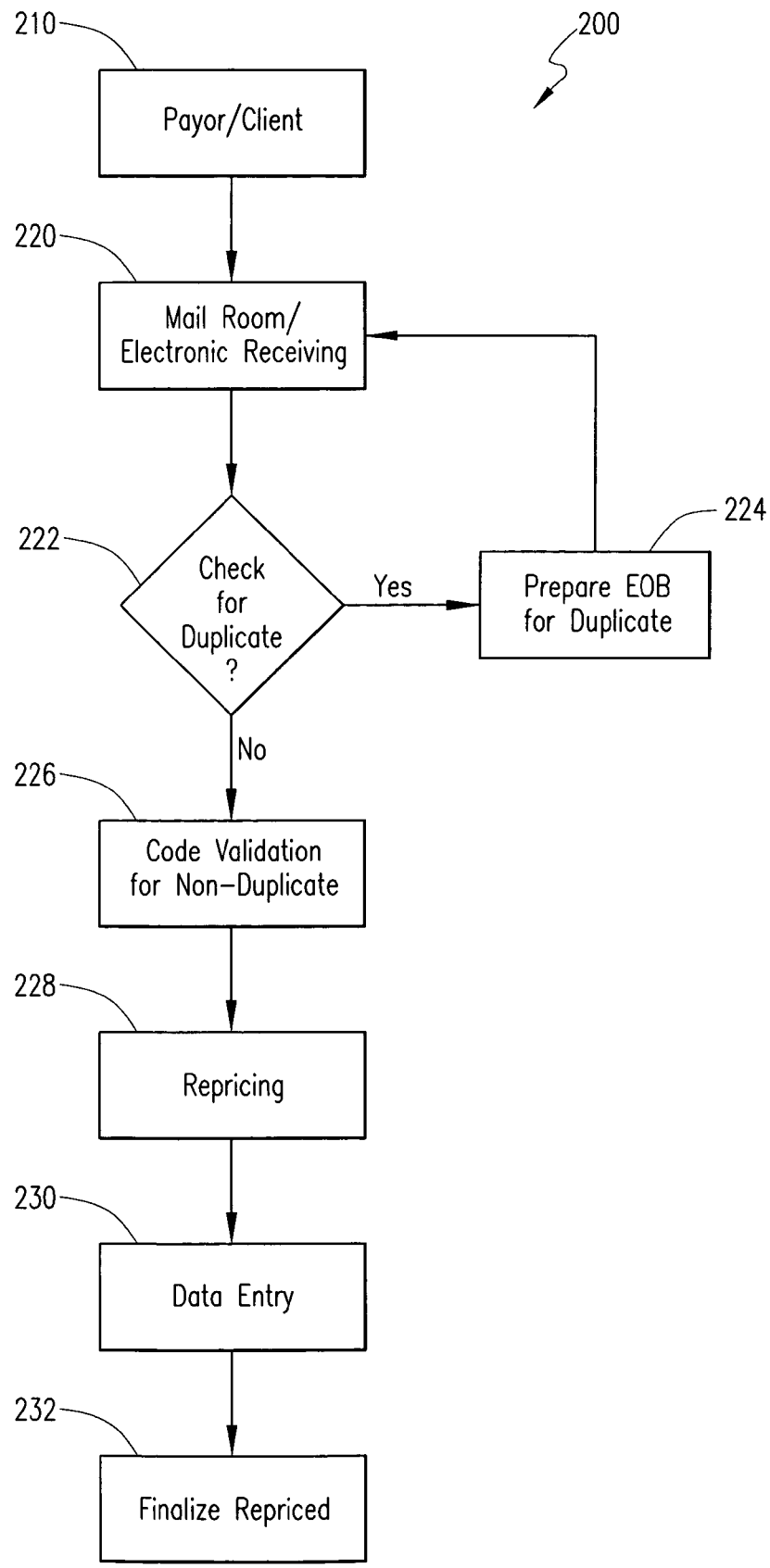
FIG. 2 is a flow diagram of a method for reviewing medical bills in accordance with principles of the present invention.

Referring now to FIG. 2, there is illustrated a flow diagram 200 of a method for reviewing medical service provider bills in accordance with principles of an exemplary MAARS method. Although the steps of the method are depicted in a particular sequence, it will be appreciated by persons of ordinary skill in the art that certain steps of the method do not necessarily follow a strict sequence but can be rearranged and/or performed simultaneously.

At step 220, medical bills from the payor/client (step 210) are received by the MAARS system 200. According to an exemplary embodiment, a single bill or a plurality of bills may be received by the MAARS system 200 at the same time. However, for purposes of simplicity, the method of reviewing the medical bills with respect to a single bill will be described.

The data from a medical bill received at the mail room or a means for electronically receiving the bill 220 is imported into a MAARS database. According to an exemplary embodiment, the medical bill is scanned into the MAARS system database by means of any ordinary scanner 220. After the bill has been scanned, certain important information related to the bill are entered into the MAARS system 200. According to an exemplary embodiment, certain important fields (e.g., client name and patient name) are entered into the exemplary MAARS system 200 by a data entry device or personnel. The bill or data received from electronic means is then sorted according to the client name and the day the bill was received. Sorting helps organize the bills according to the different clients and entities. The bill may be batched together with other bills from the same client and forwarded to at least one of the MAARS systems representatives responsible for performing the MAARS system specialty bill review.

At step 222, a MAARS system representative or electronic device reviews the bill to determine if the bill under review is a duplicate bill or if a partial or total payment has been made on the bill. If it is determined that the entire bill has been paid (step 222), the MAARS representative or electronic device software prepares an Explanation Of Review (EOR) indicating that the bill has been paid (step 224). The EOR (or the comparable data in electronic form) is sent to the mail room (or via electronic mail), which later forwards the EOR to the client. However, if it is determined at step 222 that no payment has been made on the bill in review or only a partial payment has been made, then at step 226, the MAARS representative or computer system software recalculates the bill for only portions of the bill for which no payment has been made. The MAARS representative reviews the bill extensively to determine if the bill includes inappropriate charges. MAARS representatives determine whether the diagnosis and the procedures performed were appropriate with normal standards and then verify that the bills represent appropriate CPT/ICD codes for the medical services rendered. More specifically, the MAARS system representative checks for any discrepancies in the bill that may inflate charges for the medical services provided by the MSP's.

At step 228, the MAARS system representatives or system software recalculates the medical bills using an exemplary MAARS system method. The MAARS system method utilizes multivariate time series analysis based upon:

1. Legal and regulatory findings to;
2. Cost of providing the service for comparable providers in a particular geographic region;
3. The average reimbursement being paid by all payors to medical service providers in a particular geographic region for comparable services; and
4. Reasonable charges for the actual and appropriate services provided in a particular geographic region;
5. Cost to that provider for rendering the service;
6. Average profit margin for that provider; and
7. Average profit margin for comparable providers in the area.

MAARS specialty reviews are based on a in-depth analysis of the legal and regulatory findings and case-law that are applicable to the bill because of the bill's jurisdiction and payer-type (workers' compensation, auto, ERISA, state-insurance plan, etc,). These regulatory findings being continually up-dated to factor in the most current legislation, rulings and case-law. These findings are mathematically quantified to be parameters that dictate the possible appropriate methods, given the jurisdiction and payer-type, for analyzing the charges on the bill and determining the appropriate payment for the valid billed charges.

MAARS specialty reviews uses multiple data bases and industry-references to calculate the fully-loaded costs (both direct and indirect costs) of providing the service, that are incurred by comparable providers in a particular geographic region. Using multiple data bases and independent methods to analyze and calculate costs, assures that these projections are highly reliable. In addition, MAARS uses multiple data bases and industry-references to calculate the profit-margin (over and above the cost of providing the service) that are enjoyed by the provider that submitted the bill and/or comparable providers in a particular geographic region. These findings become the minimum reference point for MAARS projections of the appropriate amount to pay in a specific jurisdiction and for a specific payer-type.

MAARS specialty reviews uses multiple data bases and industry-references to calculate the average payment being paid by all payors to medical service providers in a particular geographic region for comparable services. The amounts that other payors actually pay, as distinguished from the amounts the medical service provider bills, serve as an indicator of the market value of those services. Using multiple data bases and independent methods to analyze and calculate this average payment amount, assures that these projections are highly reliable. These findings are a reference point for MAARS projections of the appropriate amount to pay in a specific jurisdiction and for a specific payer-type.

The MAARS system reviews the documentation supporting the MSP's itemized invoice to verify that the services, devices and goods billed were actually utilized in treating the claimant. The MAARS system also compares the supporting documentation with the itemized billing to identify any billed services incongruent with the diagnosed condition.

The MAARS method is state-specific pursuant to each state's legislative records, published guidelines, rules, administrative notices and each state's case laws. In addition, the MAARS method utilizes applicable federal legislative records, published records, published guidelines, rules, administrative notices and federal case laws. Furthermore, the MAARS method uses a plurality of proprietary databases and mathematical algorithms that have never before been applied or used in medical pricing estimations to determine a reasonable amount to pay for medical bills.

While the proprietary databases are confidential, generally they are (a) compilations and mathematical analysis of data that is area-specific and procedure-specific and (b) rules for analyzing inappropriate charges. The compilations and mathematical analysis of data include area-specific and procedure-specific data on United States MSPs' costs, costs of specific MSP's for the services, the mix of payer-sources paying different types of MSPs in every United States area, the area-specific United States profit-margins of different types of MSPs, the specific profit margins of specific MSP's, the area-specific United States mark-up (over costs) of different types of MSPs, the area-specific and procedure-specific rates paid by other major payers to United States MSPs, data on the median and other percentile charges of United States MSPs' that is area-specific and procedure-specific. The rules and hierarchical ordering of the rules for analyzing inappropriate charges are based on extensive proprietary research and analysis of rules published by United States Federal, United States state, United States and foreign medical professional organizations and publications, managed care organizations, actuarial, and other establishments with specialized medical expertise.

At step 230, the recalculated bill is entered into the MAARS system and an EOR is generated. The EOR indicates a recalculated amount of reimbursement for the medical bill. The reimbursement amount includes the actual cost of medical services provided by the MSP as determined by the MAARS system plus a reasonable mark-up. The recalculated bill along with the EOR is sent to another MAARS system representative (step 232) for a quality-assurance review to ensure that the payment for the valid charges on the medical bill has been properly recalculated before being forwarded to the client.

Although preferred embodiment(s) of the method and business technique of embodiments of the present invention have been illustrated in the accompanying Drawings and described in the foregoing Detailed Description, it is understood that the present invention is not limited to the embodiment(s) disclosed, but is capable of numerous rearrangements, modifications, and substitutions without departing from the spirit of the invention as set forth and defined by the following claims.

What is claimed is:

1. A computerized medical billing review system for reviewing and recalculating a previously provided medical bill for each medical service performed in a geographical region, the previously provided medical bill being a medical bill that was generated by a medical service provider and provided to a reimbursing party, the system comprising:
    a computer system readable data storage medium;
    a computer system electronically coupled to the computer system readable data storage medium; and
    a plurality of instructions stored on the computer system readable data storage medium, wherein at least a portion of the instructions are configured to cause the computer system to:
        identify erroneous charges on the previously provided medical bill and calculate an estimated cost of the medical service/medical supply costs based on the identified erroneous charges being excluded from the previously provided medical bill;
        determine if the previously provided medical bill includes one or more medical service cost/medical supply costs making it eligible for performance of a substantive analysis based on (a) whether a jurisdiction specific legal and regulatory finding does not define a payment amount for the medical service/medical supply cost provided by the medical service provider, (b) whether an applicable fee schedule, associated with the medical service/medical supply costs exists and (c) whether rules for applying an applicable fee schedule allow for medical service providers to manipulate billing to obtain additional payments for the medical service medical supply costs;
        when it is determined that the previously provided medical bill is not eligible for performance of a substantive analysis then indicate that the reimbursing party be informed;
        when it is determined that the medical bill is eligible for performance of the substantive analysis, then perform the substantive analysis of the medical service/medical supply costs on the previously provided medical bill, the substantive analysis utilizing updated data from:
            a) a jurisdiction specific legal and regulatory findings data base comprising jurisdiction specific legal and regulatory findings data applicable to the previously provided medical bill;
            b) a cost of providing medical services data base, comprising cost of providing a same medical service by a plurality of medical service providers in a same geographical region data;
            c) a profit margin database comprising profit margin data of the same medical services/medical supplies provided by the medical service provider; and
            d) the profit margin data base further comprising profit margin data of the same medical services/medical supplies provided by a plurality of medical service providers in the same geographical location region for the same medical services/medical supplies; the data bases being stored on the computer system readable medium;
        recalculate an estimated cost for the medical service and medical service costs provided by the medical service provider based on the results of the substantive analysis; and
        provide a payment recommendation, for the reimbursing party to pay the medical service provider, for the medical services/medical supply costs on the previously provided medical bill based upon a combination of the estimated cost and the substantive analysis of the medical service/medical supply costs on the previously provided medical bill and the estimated cost.

2. The system of claim 1, wherein the profit margin data of the same medical service by the plurality of medical service providers in the same geographical region is based in part on the plurality of medical service provider's publicly filed Medicare cost reports for the same medical service.

3. The system of claim 1, wherein the estimated cost for the medical service and the payment recommendation are further determined utilizing a plurality of databases and industry references stored on the computer system readable medium.

4. The system of claim 1, wherein the system utilizes an average of amounts being charged by the plurality of medical service providers in the same or similar geographical region for the same medical service and wherein the average of amounts is stored on the computer system readable medium and incorporated into the instructions for use on a next medical bill analysis.

5. The system of claim 1, wherein the substantive analysis is utilized to determine an average payment being paid to the plurality of medical service providers in the same geographic region for a comparable medical service.

6. A computerized medical billing review system for reviewing and recalculating a previously provided medical bill for a medical service, the medical service being generated by a medical service provider in a geographical region, the system comprising:
    a data input device for electronically entering information from the previously provided medical bill;
    a computer system readable data storage medium configured to store information from the previously provided medical bill;
    a computer system being electronically coupled to the computer system readable data storage medium; and
    a plurality of instructions stored on the computer system readable data storage medium wherein the instructions are configured to cause the computer system to:
        identify erroneous medical service/medical supply charges from the previously provided medical bill;
        calculate an estimated cost of the medical service/medical supply costs based on the identified erroneous medical service/medical supply charges being excluded from the previously provided medical bill;
        determine if the previously provided medical bill includes one or more medical service cost/medical supply costs making it eligible for performance of a substantive analysis based on (a) whether a jurisdiction specific legal and regulatory finding does not define a payment amount for the medical service/medical supply cost provided by the medical service provider, (b) whether an applicable fee schedule, associated with the medical service/medical supply costs exists and (c) whether rules for applying an applicable fee schedule allow for medical service providers to manipulate billing to obtain additional payments for the medical service/ medical supply costs;

when it is determined that the previously provided medical bill is not eligible for performance of a substantive analysis then indicate that the reimbursing party be informed;

when it is determined that the medical bill is eligible for performance of the substantive analysis, then perform the substantive analysis of the medical service/medical supply costs on the previously provided medical bill, the substantive analysis utilizing updated data from a plurality of data bases including:
  a) jurisdiction specific legal and regulatory requirements stored in a data base on the computer system readable medium;
  b) industry reference data bases stored on the computer system readable medium, data in the industry reference data bases comprising previously calculated fully-loaded costs for providing the medical service/medical supplies by comparable medical service providers in the geographical region;
  c) a database containing a compilation of mathematical analysis results of geographical region specific and medical procedure specific data from previously analyzed medical bills;

determine a recalculated cost for the medical services/medical supplies provided by the medical service provider based on the results of the substantive analysis and the estimated cost when the medical bill is determined to be eligible for the substantive analysis; and provide a payment recommendation for the previously provided medical bill based upon the determined recalculated cost.

7. The system of claim 6, wherein the previously provided medical bill comprises procedure codes related to the medical services provided.

8. The system of claim 7, wherein the procedure codes are Common Procedural Codes (CPT).

9. The system of claim 8, wherein the erroneous charges include an inappropriate CPT code for the medical service provided by the medical service provider.

10. The system of claim 9, wherein the inappropriate CPT code includes at least one of a charge for services not received by a patient, a duplicate charge, a bundled charge, an erred unbundled charge, and an exploded charge.

11. The system of claim 9, wherein the inappropriate CPT code is related to a procedure not received by a patient.

12. The system of claim 7, wherein the procedure codes are International Classification of Diseases codes (ICD).

13. The system of claim 12, wherein the erroneous charges include an inappropriate ICD procedure code for the medical services provided by the medical service providers.

14. The system of claim 13, wherein the inappropriate ICD procedure code includes at least one of charges for services not received by a patient, a duplicate charge, an unbundled charge, and an exploded charge.

15. The system of claim 6, wherein the previously provided medical bill is adjusted according to one or more data bases comprising medical industry billing rules related to a state-specific legislative record, a law, a regulation, an administrative notice, and case law.

16. The system of claim 6, wherein the substantive analysis is performed by modeling:
  past, recent and historical data from the plurality of databases.

17. The system of claim 6, wherein the system is used to review medical service provider bills wherein a payer is at least one of a group health insurance plan, a group health ERISA plan, a self-funded plan, a federal or state-mandated program for paying for health care services provided to employee-related groups, an association, and an individual.

18. The system of claim 6, wherein the instructions are further configured to cause the computer to use Kalman filter algorithms to predict future payment recommendations for the medical service in the geographic region.

* * * * *